(12) United States Patent
Baschnagel

(10) Patent No.: US 8,137,294 B2
(45) Date of Patent: Mar. 20, 2012

(54) TWO-PIECE BANDAGE SYSTEM, SWAB AND COTTON PRODUCT

(76) Inventor: Robert J. Baschnagel, Garden City, NY (US)

( * ) Notice: Subject to any disclaimer, the term of this patent is extended or adjusted under 35 U.S.C. 154(b) by 88 days.

(21) Appl. No.: 12/472,672

(22) Filed: May 27, 2009

(65) Prior Publication Data

US 2010/0305491 A1 Dec. 2, 2010

(51) Int. Cl.
*A61F 13/00* (2006.01)
(52) U.S. Cl. ............... 601/42; 602/42; 602/56
(58) Field of Classification Search .......... 604/1–3; 401/37–39, 132–135, 192, 196; 602/41–54
See application file for complete search history.

(56) References Cited

U.S. PATENT DOCUMENTS

| | | | | |
|---|---|---|---|---|
| 3,757,782 A | * | 9/1973 | Aiken | 604/3 |
| 4,740,194 A | * | 4/1988 | Barabino et al. | 604/3 |
| 4,799,815 A | * | 1/1989 | Barabino et al. | 401/132 |
| 5,827,200 A | * | 10/1998 | Caillouette | 600/584 |
| 6,283,933 B1 | * | 9/2001 | D'Alessio et al. | 604/3 |
| 6,521,572 B2 | * | 2/2003 | Perlman | 510/118 |
| 6,673,031 B2 | * | 1/2004 | Mark | 604/1 |
| 2001/0051781 A1 | | 12/2001 | Augustine et al. | |
| 2005/0080368 A1 | | 4/2005 | Hurwitz | |
| 2005/0171462 A1 | | 8/2005 | Tsaur | |
| 2008/0269657 A1 | | 10/2008 | Brenneman et al. | |

OTHER PUBLICATIONS

International Search Report dated Feb. 24, 2011 and Written Opinion of the International Searching Authority.

* cited by examiner

*Primary Examiner* — Michael A. Brown
(74) *Attorney, Agent, or Firm* — Scully, Scott, Murphy & Presser, P.C.

(57) ABSTRACT

A bandage for covering an affected area of the skin is provided. The bandage including: a first bandage having an adhesive for adhering to the skin and an opening for exposing the affected area; a second bandage for covering the opening; and a releasable attachment system for releasably securing the second bandage to the first bandage to cover the opening. Also provided is a swab including: a tubular body having a conduit and a breakable wall portion disposed in the conduit; a fluid disposed in the conduit; and a cotton swab disposed at an end of the tubular body; wherein bending of the tubular body breaks the breakable wall portion allowing the fluid to flow into the cotton swab. Still further provided is a cotton product including: a cotton body; and a breakable capsule disposed in the body, the breakable capsule having a cavity filled with a fluid.

10 Claims, 2 Drawing Sheets

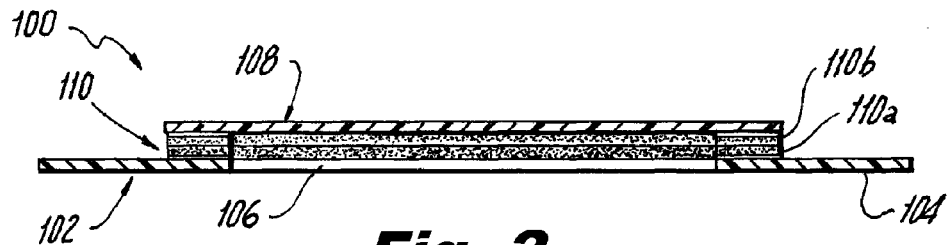
Fig. 2
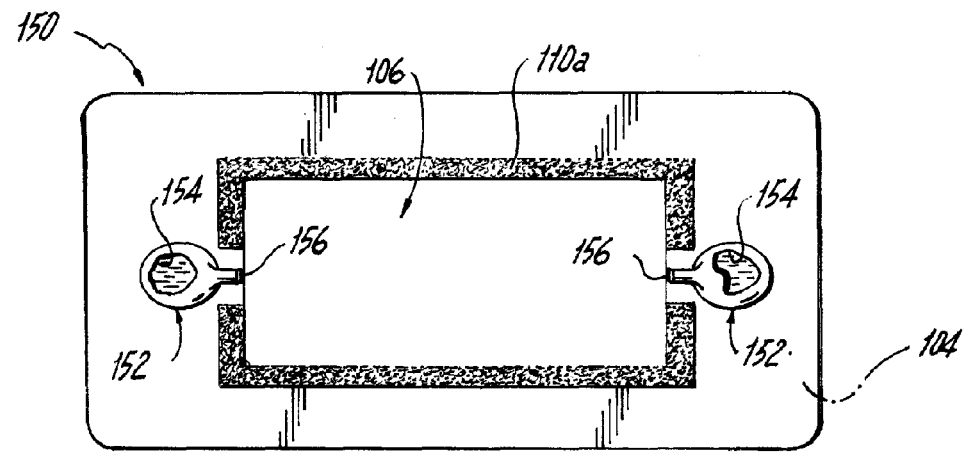
Fig. 3
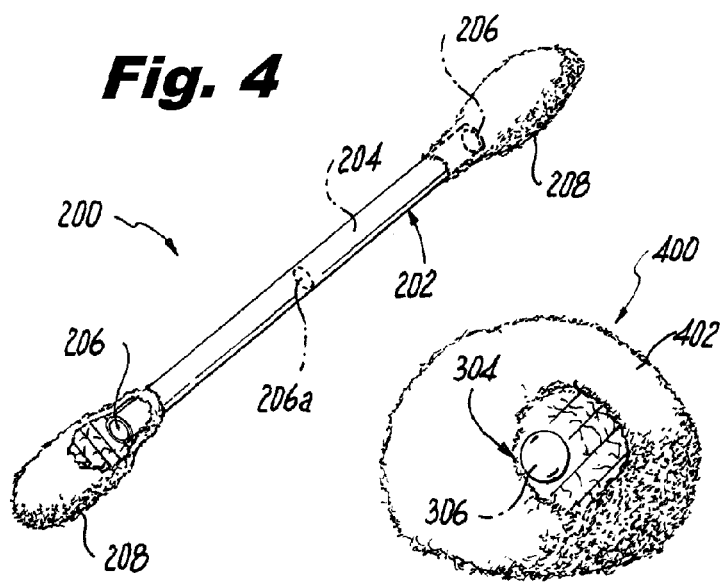
Fig. 4
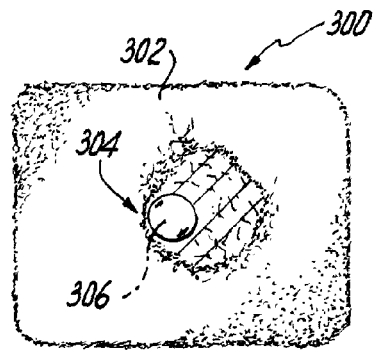
Fig. 5a
Fig. 5b

TWO-PIECE BANDAGE SYSTEM, SWAB AND COTTON PRODUCT

BACKGROUND

1. Field

The present invention relates generally to bandages and cotton products and, more particularly, to a two-piece bandage system, a cotton swab and a cotton product.

2. Prior Art

Adhesive bandages are well known in the art. Such bandages typically have a pair of adhesive portions on each side of a gauze pad. The gauze pad is positioned on an affected area of the skin, such as a scrape or cut and the adhesive portions hold the gauze pad in place. However, if the affected area of the skin is to be examined, such adhesive bandages must be removed and discarded. If the affected area is not sufficiently healed and an adhesive bandage is still required, a new adhesive bandage must be used in place of the discarded one. Furthermore, the gauze pad is typically in contact with the affected area of the skin and tends to rub off any medicament on the affected area, can irritate the affected area and prevents airflow to the affected area.

SUMMARY

Accordingly, a bandage for covering an affected area of the skin is provided. The bandage comprising: a first bandage portion having an adhesive for adhering to the skin and an opening for exposing the affected area; a second bandage portion for covering the opening; and a releasable attachment means for releasable securing the second bandage portion to the first bandage portion to cover the opening.

The releasable attachment means can comprise a hook and loop fastener wherein a hook portion of the hook and loop fastener is attached to one of the first bandage portion and second bandage portion and a loop portion of the hook and loop fastener is attached to the other of the first bandage portion and second bandage portion.

The bandage can further comprise medicament storage and application means for storing medicament and applying the medicament into the opening to the affected area. The medicament storage and application means can comprise one or more containers having a cavity to hold the medicament, the cavity being in fluid communication with an outlet disposed adjacent to the opening such that pressure applied to the containers causes the medicament in the cavity to flow out of the outlet and onto the affected area. The outlet can include a valve. The valve can be a one-way valve.

The container can be formed at least in part of a plastic material or of a metallic foil.

The one or more containers can comprise two containers.

Also provided is a swab comprising: a tubular body having a conduit and at least one breakable wall portion disposed in the conduit; a fluid disposed in the conduit; and at least one cotton swab disposed at an end of the tubular body; wherein bending of the tubular body breaks the breakable wall portion thereby allowing the fluid to flow into the cotton swab.

The at least one cotton swab can comprise two cotton swabs disposed at each of two ends of the tubular body; and the at least one breakable wall portion can comprise two breakable wall portions, each of which is broken by the bending of the tubular body thereby allowing the fluid to flow into each of the two cotton swabs.

The fluid can be a medicament, such as peroxide or a beauty aid, such as nail polish remover.

Still further provided is a cotton product comprising: a cotton body portion; and a breakable capsule disposed in the body portion, the breakable capsule having a cavity filled with a fluid.

The cotton body portion can be one of a gauze sheet and a cotton ball.

The fluid can be a medicament, such as peroxide or a beauty aid, such as nail polish remover.

BRIEF DESCRIPTION OF THE DRAWINGS

These and other features, aspects, and advantages of the apparatus and methods of the present invention will become better understood with regard to the following description, appended claims, and accompanying drawings where:

FIG. 2 illustrates a sectional view of the bandage system of FIG. 1c as taken along sectional line 2-2.

FIG. 3 illustrates a variation of the embodiment of the first bandage portion of the bandage system of FIG. 1a.

FIG. 4 illustrates a top view of an embodiment of a swab.

FIG. 5a illustrates a top view of an embodiment of a cotton product in the form of a gauze sheet.

FIG. 5b illustrates a top view of an embodiment of a cotton product in the form of a cotton ball.

DETAILED DESCRIPTION OF THE PREFERRED EMBODIMENT

Figure 1A:
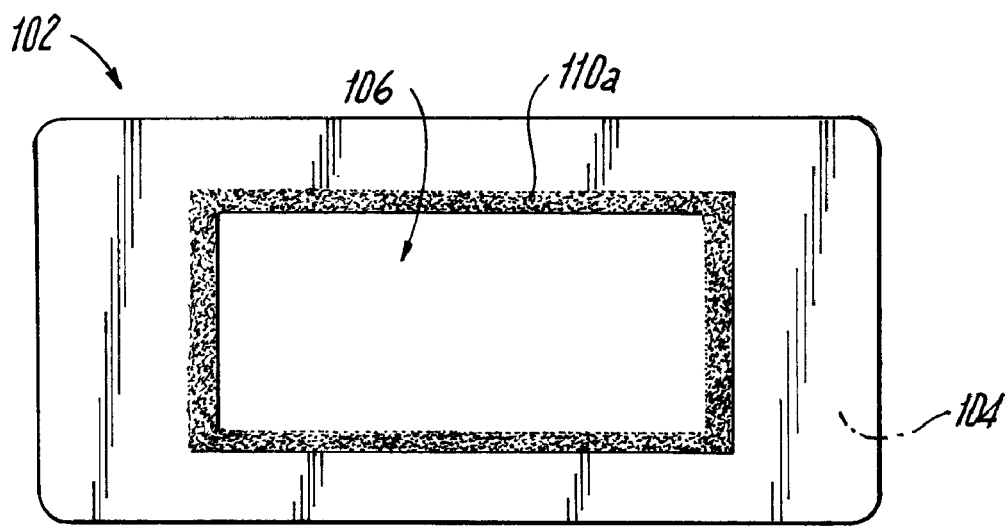
FIG. 1a illustrates a top view of a first bandage portion of an embodiment of a bandage system.

Referring now to FIGS. 1a-1c and 2, there is shown a bandage for covering an affected area of the skin, the bandage being generally referred to by reference numeral 100. As shown in FIG. 1a, the bandage includes a first bandage portion 102 having an adhesive 104 for adhering to the skin. The first bandage portion 102 is made of well know bandage materials known in the art, such as thin plastic sheets or gauze. The adhesive 104 is disposed on a surface opposite to the surface shown in FIG. 1a (referred to as the back surface which is the surface which contacts the skin). Such adhesives are well known in the bandage art and can be coated on the entire back surface of the first bandage portion 102 or a portion thereof, such as around a perimeter of the first bandage portion 102. As is also well known in the bandage arts, a sheet, such as a plastic or wax sheet (not shown) can be provided over the adhesive to prevent the adhesive from inadvertently adhering to an unintended surface until it is ready to be applied to the skin. The first bandage portion 102 further has an opening 106 for exposing the affected area of the skin. Thus, the first bandage portion 102 is adhered around the affected area, with the affected area being exposed through the opening 106. The affected area can have any type of skin condition or rash, such as impetigo, eczema, rosea, and psoriasis.

Figure 1B:
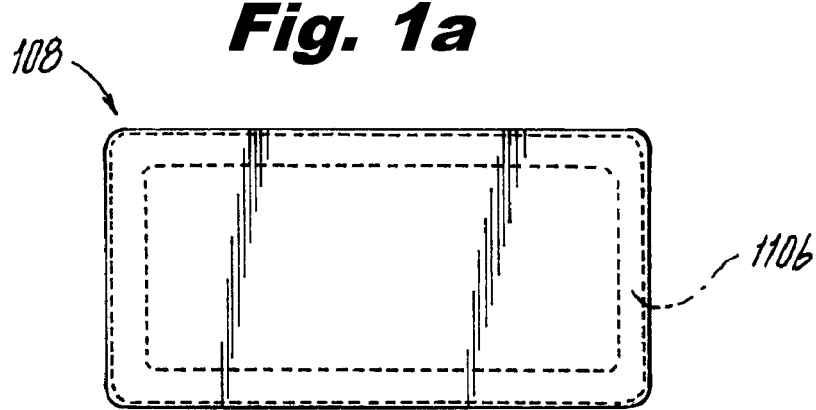
FIG. 1b illustrates a top view of a second bandage portion of an embodiment of a bandage system.
Figure 1C:
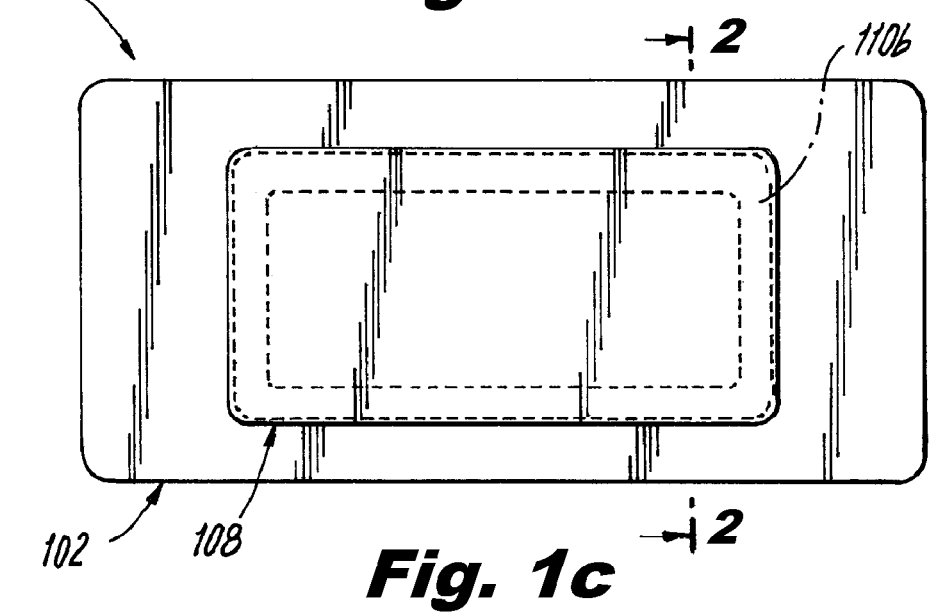
FIG. 1c illustrates a top view of the first and second bandage portions of FIGS. 1a and 1b forming an embodiment of the bandage system.

Referring now to FIG. 1b, there is shown a second bandage portion 108 for covering the opening 106. The second bandage portion 108 is also made of well know bandage materials known in the art, such as thin plastic sheets or gauze. A releasable attachment means for releasably securing the second bandage portion 108 to the first bandage portion 102 to cover the opening 106 is also provided. FIG. 1c illustrates the second bandage portion 108 being secured over the opening 106 of the first bandage portion 102. The releasable attachment means can comprise a hook and loop fastener 110 wherein a hook portion 110*a* of the hook and loop fastener 110 is attached to an upper surface (opposite the surface to which the adhesive 104 is disposed) of the first bandage portion 102 and a loop portion 110*b* of the hook and loop fastener 110 is attached to the second bandage portion 108. Although the hook and loop portions 110*a*, 110*b* are shown disposed around the entire periphery of the opening 106; they can also be disposed around a portion thereof. Of course, the hook portion 110*a* can be disposed on the second bandage portion 108 and the loop portion disposed on the first bandage portion 102.

Thus, the first bandage portion 108 can be affixed to the skin so as to have an affected area exposed through the opening 106 and the second bandage portion 108 can be removably attached to the first bandage portion 108. By such a configuration, the affected area can be repeatedly treated with medicament, ointments and the like without removing the bandage. The second bandage portion 108 is simply removed from the first bandage portion 102, the affected area treated and the second bandage portion re-attached to the first bandage portion 102 to shield the affected area from the environment. Such a procedure can be repeated until the affected area has healed or until the bandage 100 is no longer desired. Alternatively, only the second bandage portion 108 can be discarded and replaced after being removed.

Other releasable attachment means are also possible as long as the second bandage portion 108 can be removed from the first bandage portion 102 to expose the affected area of the skin through the opening 106 and the second bandage portion 108 (or a new second bandage portion 108) can be reattached to the first bandage portion 102 after the treatment of the affected area. For example, the releasable attachment means can be releasable adhesive, such as that well known in the art of memo pads (self-stick removable notes). The releasable attachment means can also be a mechanical type releasable fastener, such as a string attached to one of the first and second bandage portions 102, 108 which wraps around a small protrusion (e.g., button) disposed on the other of the first and second bandage portions 102, 108.

Referring now to FIG. 3, there is shown a variation of the first bandage portion of FIG. 1*a*, generally referred to by reference numeral 150, where like features are designated by like reference numerals. The first bandage portion 150 of FIG. 3 includes medicament storage and application means for storing medicament and applying the medicament into the opening 106 to the affected area. The medicament can be any medicine or ointment or other fluid useful in treating the affected area of the skin. The medicament storage and application means can comprise one or more containers 152 having a cavity 154 to hold the medicament where the cavity 154 is in fluid communication with an outlet 156 disposed adjacent to the opening 106 such that pressure applied to the containers 152 causes the medicament in the cavity 154 to flow out of the outlet 156 and onto the affected area. The container 152 can be any known in the art, such as similar to a toothpaste tube where the outlet has a cap type plug that can be pulled off to allow the medicament to be dispensed through the outlet 156. Such toothpaste type containers are well known in the art and can be made of plastic, a metallic foil, such as aluminum, or a laminate of both. The container 152 can also be a gel type capsule having a weakened portion acting as the outlet, such that pressure applied to the gel type capsule causes the weakened portion to rupture. The container 152 can also be resilient to the applied pressure such that the medicament is dispensed from the outlet when the pressure is applied and the container regains its original form after the pressure is removed to stop the flow of medicament. Such resilient containers can be made at least partly of a plastic material. The outlet 156 can also have a valve so as to prevent the medicament from being dispensed unless the valve is opened. The valve can be opened by the application of pressure to the container 152, such as with a one-way valve. Such one-way valves are well known in the art, such as a duckbill valve. Lastly, the medicament can be dispensed all at once or a little at a time. Alternatively, the container(s) can be disposed on the second bandage portion 108.

Thus, medicament can be applied, and re-applied to the affected area from the containers 102. The medicament can be applied with or without removing the second bandage portion 108. Furthermore, as shown in FIG. 2, the second bandage portion 108 can be configured to be raised above the surface of the skin so as not to contact the skin. Such a configuration allows the medicament to stay on the affected area longer without being rubbed off and also allows air to enter the affected area.

Referring now to FIG. 4, there is shown a swab, generally referred to by reference numeral 200. Swabs are well known in the art, such as for cleaning ear wax from the ear canal, removing nail polish from nails or cleaning delicate parts with solvents and/or cleaners to name a few. The swab 200 has a tubular body 202 having a conduit 204. The tubular body 202 is flexible and resilient so that it can be bent without breaking or being damaged. The tubular body 202 can be made of a plastic.

The tubular body 202 includes at least one breakable wall portion 206 disposed in the conduit 204. Such breakable wall portions 206 are well known in the art, such as those used in light sticks that, when bent, the breakable wall portions are broken allowing the fluids therein to mix and become luminescent.

A fluid is disposed in the conduit 204 and one or more cotton swabs 208 are disposed on one or both of the ends of the tubular body 202. As with light sticks known in the art, bending of the tubular body 202 breaks the breakable wall portions 206. After the breakable wall portions 206 are broken, the fluid is allowed to flow into the cotton swabs 208.

The breakable wall portions 206 can be disposed near the ends of the tubular body 202 such that, when broken, the fluid can flow into each of the two cotton swabs 208. If only a single cotton swab 208 is used, one end of the tubular body 202 is plugged or otherwise closed and the other end having the cotton swab 208 includes a breakable wall portion 206. One or more additional breakable wall portions 206*a* can be provided to also allow two or more fluids to mix upon breaking, such as a two-part epoxy that can mix and be applied with the cotton swab 208.

As discussed above, the fluid can be a medicament, such as peroxide or a beauty aid, such as nail polish remover. The fluid is not limited to medicaments and beauty aids and can be anything useful with a cotton swab Referring now to FIGS. 5*a* and 5*b*, there are shown cotton products, generally referred to by reference numerals 300 and 400, respectively. The cotton products comprise a cotton body portion. In the case of FIG. 5*a*, such cotton body portion is configured as a gauze sheet 302, while in FIG. 5*b*, the cotton body portion is configured as a cotton ball 402. Such cotton body portions are shown by way of example only. Those skilled in the art will appreciate that the cotton body portions can take many other shapes and forms.

The cotton body portion includes a breakable capsule 304 disposed therein. The capsule 304 can be on a surface of the cotton body portion or partly or fully embedded therein. The breakable capsule 304 has a cavity 306 filled with a fluid. The fluid can be any fluid useful with a cotton product, such as a medicament like peroxide or a beauty aid like nail polish remover.

Breakable capsules 304 are well known in the art and are broken to release the fluid therein when a sufficient pressure is applied to the capsule body. Thus, when the cotton product is to be used, the user can squeeze the cotton body product to apply pressure to the capsule 304 to rupture the capsule 304 and release the fluid therein into the cotton body portion.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A cotton product comprising:
   a cotton body portion; and
   a breakable capsule disposed in the body portion, the breakable capsule having a cavity filled with a fluid;
   wherein the cotton body portion is a gauze sheet.

2. The cotton product of claim 1, wherein the fluid is a medicament.

3. The cotton product of claim 2, wherein the medicament is peroxide.

4. The cotton product of claim 1, wherein the fluid is a beauty aid.

5. The cotton product of claim 4, wherein the beauty aid is nail polish remover.

6. A cotton product comprising:
   a cotton body portion; and
   a breakable capsule disposed in the body portion, the breakable capsule having a cavity filled with a fluid;
   wherein the cotton body portion is a cotton ball.

7. The cotton product of claim 6, wherein the fluid is a medicament.

8. The cotton product of claim 7, wherein the medicament is peroxide.

9. The cotton product of claim 6, wherein the fluid is a beauty aid.

10. The cotton product of claim 9, wherein the beauty aid is nail polish remover.

* * * * *